United States Patent
Novkov

(10) Patent No.: US 11,872,349 B2
(45) Date of Patent: Jan. 16, 2024

(54) SYSTEMS AND METHODS FOR INCREASING VENTILATOR OXYGEN CONCENTRATION

(71) Applicant: Covidien LP, Mansfield, MA (US)

(72) Inventor: Donald J. Novkov, Encinitas, CA (US)

(73) Assignee: Covidien LP, Mansfield, MA (US)

( * ) Notice: Subject to any disclaimer, the term of this patent is extended or adjusted under 35 U.S.C. 154(b) by 282 days.

(21) Appl. No.: 17/224,604

(22) Filed: Apr. 7, 2021

(65) Prior Publication Data

US 2021/0316104 A1 Oct. 14, 2021

Related U.S. Application Data

(60) Provisional application No. 63/008,508, filed on Apr. 10, 2020.

(51) Int. Cl.
*A61M 16/12* (2006.01)
*A61M 16/10* (2006.01)
(Continued)

(52) U.S. Cl.
CPC ...... *A61M 16/125* (2014.02); *A61M 16/0066* (2013.01); *A61M 16/101* (2014.02);
(Continued)

(58) Field of Classification Search
CPC .............. A61M 16/0066; A61M 16/10; A61M 16/1005; A61M 16/12; A61M 16/122;
(Continued)

(56) References Cited

U.S. PATENT DOCUMENTS

| 3,605,785 A | 9/1971 | Dobritz |
| 4,141,354 A | 2/1979 | Ismach |

(Continued)

FOREIGN PATENT DOCUMENTS

| EP | 482261 | 4/1992 |
| WO | 9107912 | 6/1991 |

(Continued)

OTHER PUBLICATIONS

7200 Series Ventilator, Options, and Accessories: Operator's Manual. Nellcor Puritan Bennett, Part No. 22300 A, Sep. 1990, pp. 1-196.
(Continued)

*Primary Examiner* — Joseph D. Boecker

(57) ABSTRACT

Methods and systems for increasing oxygen concentration. An example system includes an oxygen valve configured to be coupled to an oxygen source, an oxygen plenum coupled to the valve, and a mixing valve. The mixing valve includes an oxygen inlet coupled to the oxygen plenum, an ambient-air inlet, and an outlet configured to be attached to an inlet of a blower of a ventilator. The system also includes a pressure sensor, coupled to the oxygen plenum, and a control device communicatively coupled to the pressure sensor and the oxygen valve. The control device receives a differential pressure, measured by the pressure sensor, and based on the measured differential pressure, generates a control signal to control the oxygen valve to maintain a target pressure of gas within the oxygen plenum.

16 Claims, 4 Drawing Sheets

(51) Int. Cl.
*A61M 16/00* (2006.01)
*A61M 16/20* (2006.01)

(52) U.S. Cl.
CPC ........ *A61M 16/1005* (2014.02); *A61M 16/12* (2013.01); *A61M 16/203* (2014.02); *A61M 16/209* (2014.02); *A61M 16/208* (2013.01); *A61M 2016/0027* (2013.01); *A61M 2016/1025* (2013.01); *A61M 2202/0208* (2013.01); *A61M 2205/3331* (2013.01); *A61M 2205/3351* (2013.01); *A61M 2205/50* (2013.01)

(58) Field of Classification Search
CPC .............. A61M 16/125; A61M 16/127; A61M 16/204; A61M 2016/0027; A61M 2016/1025
See application file for complete search history.

(56) References Cited

U.S. PATENT DOCUMENTS

| | | |
|---|---|---|
| 4,267,827 A | 5/1981 | Rauscher et al. |
| 4,340,044 A | 7/1982 | Levy et al. |
| 4,560,519 A | 12/1985 | Cerny |
| 4,602,653 A | 7/1986 | Ruiz-Vela et al. |
| 4,775,795 A | 10/1988 | Biehl et al. |
| 4,905,685 A | 3/1990 | Olsson et al. |
| 5,014,694 A * | 5/1991 | DeVries ................ A61M 16/12 128/205.24 |
| 5,044,362 A | 9/1991 | Younes |
| 5,092,326 A | 3/1992 | Winn et al. |
| 5,159,924 A | 11/1992 | Cegielski et al. |
| 5,186,167 A | 2/1993 | Kolobow |
| 5,237,987 A | 8/1993 | Anderson et al. |
| 5,255,675 A | 10/1993 | Kolobow |
| 5,299,568 A | 4/1994 | Forare et al. |
| 5,299,579 A | 4/1994 | Gedeon et al. |
| 5,383,449 A | 1/1995 | Forare et al. |
| RE34,938 E | 5/1995 | Serikov et al. |
| 5,452,714 A | 9/1995 | Anderson et al. |
| 5,522,381 A | 6/1996 | Olsson et al. |
| 5,664,560 A | 9/1997 | Merrick et al. |
| 5,676,133 A | 10/1997 | Hickle et al. |
| 5,692,497 A | 12/1997 | Schnitzer et al. |
| 5,722,392 A | 3/1998 | Skimming et al. |
| 5,722,449 A | 3/1998 | Heinonen et al. |
| 5,765,558 A | 6/1998 | Psaros et al. |
| 5,823,186 A | 10/1998 | Rossen et al. |
| 5,887,611 A * | 3/1999 | Lampotang ........... A61M 16/12 137/93 |
| 5,915,834 A | 6/1999 | McCulloh |
| 5,934,274 A | 8/1999 | Merrick et al. |
| 5,954,051 A | 9/1999 | Heinonen et al. |
| 6,015,388 A | 1/2000 | Sackner et al. |
| 6,029,660 A | 2/2000 | Calluaud et al. |
| 6,076,523 A | 6/2000 | Jones et al. |
| 6,116,240 A | 9/2000 | Merrick et al. |
| 6,148,816 A | 11/2000 | Heinonen et al. |
| 6,158,434 A | 12/2000 | Lugtigheid et al. |
| 6,250,302 B1 | 6/2001 | Rantala |
| 6,279,574 B1 | 8/2001 | Richardson et al. |
| 6,390,988 B1 | 5/2002 | Robinson |
| 6,412,483 B1 | 7/2002 | Jones et al. |
| 6,467,478 B1 | 10/2002 | Merrick et al. |
| 6,659,961 B2 | 12/2003 | Robinson |
| 6,782,888 B1 | 8/2004 | Friberg et al. |
| 6,827,084 B2 | 12/2004 | Grubb, Jr. |
| 6,830,048 B2 | 12/2004 | Wruck et al. |
| 6,851,426 B1 | 2/2005 | Strömberg |
| 6,990,977 B1 | 1/2006 | Calluaud et al. |
| 7,219,666 B2 | 5/2007 | Friberg et al. |
| 7,275,540 B2 | 10/2007 | Bolam et al. |
| 7,509,957 B2 | 3/2009 | Duquette et al. |
| 7,516,742 B2 | 4/2009 | Stenzler et al. |
| 7,530,353 B2 | 5/2009 | Choncholas et al. |
| 7,610,914 B2 | 11/2009 | Bolam et al. |
| 7,779,834 B2 | 8/2010 | Calluaud et al. |
| 7,886,740 B2 | 2/2011 | Thomas et al. |
| 2001/0022181 A1 | 9/2001 | Masson et al. |
| 2003/0062045 A1 * | 4/2003 | Woodring .......... A61M 16/0051 128/204.21 |
| 2004/0200477 A1 | 10/2004 | Bleys et al. |
| 2005/0000517 A1 | 1/2005 | Eriksson et al. |
| 2006/0084931 A1 * | 4/2006 | Huang .................. A61M 16/10 604/317 |
| 2006/0231098 A1 | 10/2006 | Downie et al. |
| 2007/0125374 A1 | 6/2007 | Smith et al. |
| 2007/0125377 A1 * | 6/2007 | Heinonen ........... A61M 16/203 128/204.21 |
| 2007/0144523 A1 | 6/2007 | Bolam et al. |
| 2007/0169779 A1 | 7/2007 | Freeman |
| 2007/0181126 A1 | 8/2007 | Tolmie et al. |
| 2008/0078389 A1 | 4/2008 | Xiao et al. |
| 2008/0121233 A1 | 5/2008 | von Blumenthal et al. |
| 2008/0127975 A1 | 6/2008 | Lirsch et al. |
| 2008/0149104 A1 | 6/2008 | Eifler |
| 2008/0156328 A1 | 7/2008 | Taube |
| 2015/0328417 A1 * | 11/2015 | Löser .................. A61M 16/024 128/204.23 |
| 2016/0279378 A1 * | 9/2016 | Cipollone ......... A61M 16/0063 |
| 2021/0001075 A1 * | 1/2021 | Oddo ................ B01D 53/0454 |
| 2023/0122775 A1 * | 4/2023 | Johnson ............. A61M 16/024 128/204.21 |
| 2023/0173214 A1 * | 6/2023 | Galbraith ............ B01D 53/047 128/204.21 |

FOREIGN PATENT DOCUMENTS

| | | |
|---|---|---|
| WO | 9731670 | 9/1997 |
| WO | 9818383 | 5/1998 |
| WO | 74757 | 12/2000 |

OTHER PUBLICATIONS

7200 Ventilatory System: Addendum/Errata. Nellcor Puritan Bennett, Part No. 4-023576-00, Rev. A, Apr. 1998, pp. 1-32.
800 Operator's and Technical Reference Manual. Series Ventilator System, Nellcor Puritan Bennett, Part No. 4-070088-00, Rev. L, Aug. 2010, pp. 1-476.
840 Operator's and Technical Reference Manual. Ventilator System, Nellcor Puritan Bennett, Part No. 4-075609-00, Rev. G, Oct. 2006, pp. 1-424.
Puritan Bennett 980 Series Ventilator Operator's Manual, Covidien, Jan. 29, 2014, Part. No. 10077893 A 2014-01, 506 pages.

* cited by examiner

SYSTEMS AND METHODS FOR INCREASING VENTILATOR OXYGEN CONCENTRATION

CROSS-REFERENCE TO RELATED APPLICATIONS

This application claims the benefit of U.S. Provisional Application No. 63/008,508, filed Apr. 10, 2020, the complete disclosure of which is hereby incorporated herein by reference in its entirety.

INTRODUCTION

Medical ventilator systems are used to provide ventilatory support to patients. Some ventilators include blowers that generate pressurized air to provide to the patients. Depending on the particular condition of a patient, ambient air is enriched with oxygen and the mixture of air is provided to the patient. The oxygen concentration that is desired to be delivered to the patient may depend on the particular patient or condition of the patient.

It is with respect to these and other general considerations that the aspects disclosed herein have been made. Also, although relatively specific problems may be discussed, it should be understood that the examples should not be limited to solving the specific problems identified in the background or elsewhere in this disclosure.

SUMMARY

Examples of the present disclosure describe systems and methods for increasing oxygen concentrations for medical ventilators. In an aspect, the technology relates to a system for increasing oxygen concentration. The system includes an oxygen valve configured to be coupled to an oxygen source; an oxygen plenum coupled to the valve; and a mixing valve. The mixing valve includes an oxygen inlet coupled to the oxygen plenum; an ambient-air inlet; and an outlet configured to be attached to an inlet of a blower of a ventilator. In an example, the oxygen valve is a proportional valve. In another example, the mixing valve is one of a manual mixing valve or an electromechanical mixing valve controlled by a signal from a microprocessor based on a user setpoint. In yet another example, the system further includes a dial to control the mixing valve, wherein different settings of the dial correspond to different oxygen concentrations provided at the outlet of the mixing valve. In still another example, the system further includes a pressure sensor coupled to the oxygen plenum. In a further example, the pressure sensor is configured to measure a differential pressure between gas in the oxygen plenum and ambient air.

In another example, the system further includes a control device, the control device configured to perform a set of operations that include receiving the differential pressure measured by the pressure sensor; and based on the measured differential pressure, generating a control signal to control the oxygen valve to maintain a target pressure of gas within the oxygen plenum. In a yet another example, the measured differential pressure is below the target pressure; and the control signal is configured to open the oxygen valve. In still yet another example, the measured differential pressure is above the target pressure; and the control signal is configured to close the oxygen valve.

In another example, the target pressure is less than or equal to 0.5 inH2O. In a further example, the ambient-air inlet of the mixing valve further includes a check valve to prevent flow of oxygen from the oxygen plenum through the ambient-air inlet. In yet another example, the system further includes at least one of a check valve or a relief valve coupled to the oxygen plenum to relieve gas pressure in the oxygen plenum.

In another aspect, the technology relates to a system for increasing oxygen concentration. The system includes an oxygen valve configured to be coupled to an oxygen source, an oxygen plenum coupled to the valve, and a mixing valve. The mixing valve includes an oxygen inlet coupled to the oxygen plenum; an ambient-air inlet; and an outlet configured to be attached to an inlet of a blower of a ventilator. The system further includes a pressure sensor coupled to the oxygen plenum. The pressure sensor is configured to measure a differential pressure between gas in the oxygen plenum and ambient air. The system also includes a control device communicatively coupled to the pressure sensor and the oxygen valve. The control device is configured to perform a set of operations. The operations include receiving the differential pressure measured by the pressure sensor; and based on the measured differential pressure, generating a control signal to control the oxygen valve to maintain a target pressure of gas within the oxygen plenum.

In an example, the measured differential pressure is below the target pressure; and the control signal is configured to open the oxygen valve. In another example, the measured differential pressure is above the target pressure; and the control signal is configured to close the oxygen valve. In yet another example, the target pressure is less than or equal to 0.5 inH2O.

In another aspect, the technology relates to a method for increasing oxygen concentration. The method includes measuring, by a pressure sensor, a first differential pressure between ambient air and gas in an oxygen plenum; based on the first differential pressure, generating, by a control device, a first control signal; transmitting the first control signal to an oxygen valve to cause the oxygen valve to change position to affect flow of oxygen into the oxygen plenum; measuring, by the pressure sensor, a second differential pressure between the ambient air and gas in the oxygen plenum; based on the second differential pressure, generating, by a control device, a second control signal; and transmitting the second control signal to the oxygen valve to cause the oxygen valve to change position to affect flow of oxygen into the oxygen plenum.

In an example, generating the first control signal is further based on a comparison of the first differential pressure and a target pressure; and generating the second control signal is further based on a comparison of the second differential pressure and the target pressure. In another example, the target pressure is less than or equal to 0.5 inH2O. In yet another example, the first differential pressure is less than the target pressure and the first control signal is configured to cause the oxygen valve to open. In still another example, the second differential pressure is greater than the target pressure and the second control signal is configured to cause the oxygen valve to close. In a further example, the method also includes altering a setting of a mixing valve, coupled to the oxygen plenum, to alter an oxygen concentration provided from the mixing valve.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Additional aspects, features, and/or advantages of examples will be set forth in part in the description which follows and, in part, will be apparent from the description, or may be learned by practice of the disclosure.

BRIEF DESCRIPTION OF THE DRAWINGS

Non-limiting and non-exhaustive examples are described with reference to the following figures.

DETAILED DESCRIPTION

As discussed above, some ventilators include a blower that provides ambient air into a ventilator and ultimately to a patient. Some of these ventilators may also include an input to receive low-pressure concentrated oxygen. Such ventilators, however, may be limited in the amount of oxygen concentration that can be provided to a patient. For example, oxygen concentration that is delivered to the patient may be limited to ranges near 50% or lower. The lower oxygen concentration may not be appropriate for treating patients that have conditions that are best treated with higher oxygen concentrations, such as 95% and higher. Accordingly, an improvement to ventilators to improve oxygen concentrations is desired.

Among other benefits, the present technology provides solutions to increasing oxygen concentration in ventilators having blowers. The present technology enriches the air at the inlet of the blower with additional oxygen. Thus, when the blower is initiated, the air that is propelled by the blower has a higher concentration of oxygen, resulting in a higher concentration of oxygen ultimately provided to the patient. To provide oxygen-enriched air at the blower, the present technology may actively control pressure of an oxygen-filled plenum. The gas within the plenum is then be provided to the inlet of a blower via a mixing valve. The mixing valve may be used to set the oxygen concentration that is desired to be provided to the inlet of the blower. By actively controlling the pressure of gas in the plenum, the pressure of gas provided at the inlet of blower may be maintained to be greater than ambient pressure. In addition, the pressure of the gas in the plenum may be maintained at a level where substantial oxygen is not exhausted into the ambient air and neither the blower nor the ventilator controls are significantly affected by the gas provided from the plenum.

Figure 1:
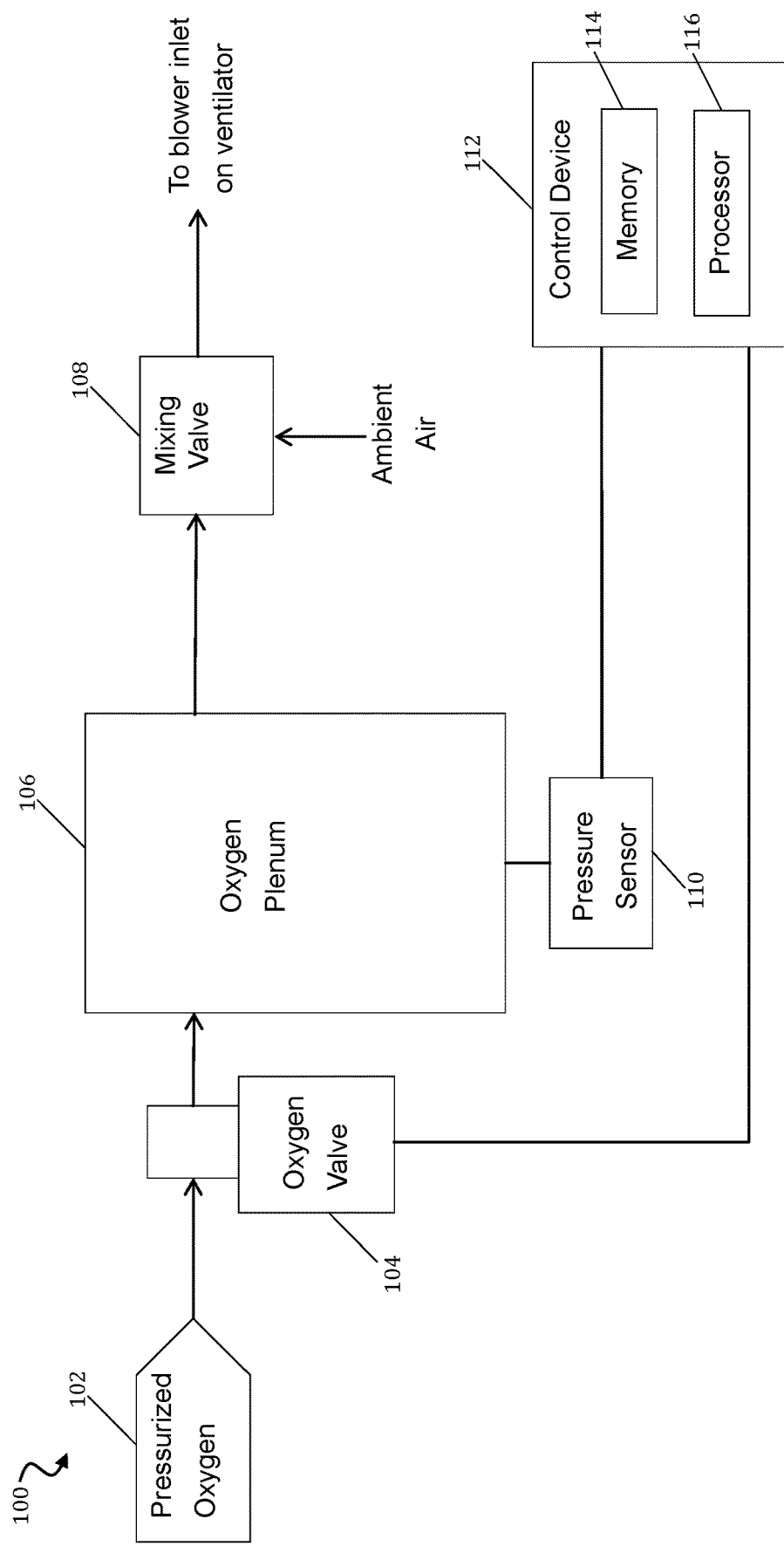
FIG. 1 depicts an example system for increasing oxygen concentration.

FIG. 1 depicts an example system 100 for increasing oxygen concentration. The system 100 may be attached or coupled to an inlet of a blower of a ventilator to increase the oxygen concentration that can be provided by the ventilator. The system 100 includes an oxygen plenum 106 that is filled or pressurized from a pressurized oxygen source 102. The flow of oxygen from the oxygen source 102 is controlled by an oxygen valve 104. The valve 104 may be any valve suitable for controlling the flow of a gas. In some examples, the valve 104 may be a proportional solenoid (PSOL) valve where the amount of flow may be proportionally regulated. In other examples, the valve 104 may be a valve that is either fully open or fully closed.

The pressure of the gas in the plenum 106 may be controlled by a control loop that includes at least a pressure sensor 110 and a control device 112. The pressure sensor 110 may measure the pressure of the gas in the plenum 106. The measure of the pressure of the gas may be relative to the ambient pressure, such as a differential pressure between ambient air and the gas in the plenum. A certain pressure for the gas in the plenum 106 may be targeted. For example, the targeted pressure may be less than about 1.0 inH$_2$O (2.52 cmH$_2$O) above the ambient pressure. In some instances, the targeted pressure for the gas in the plenum 106 may be less than or equal to about 0.5 inH$_2$O (1.27 cmH$_2$O) or less than or equal to about 0.2 inH$_2$O (0.5 cmH$_2$O). Accordingly, the targeted pressure is not substantially higher than the ambient air. The intent of the target pressure is maintain a slight pressure of gas from plenum 106 at the inlet of the blower. By maintaining a slight pressure, rather than a high pressure, a minimal amount of oxygen is wasted by being exhausted into the ambient air. In addition, high pressure gas may have a negative effect on the blower or operation of the ventilator. For example, if a high pressure gas is applied to the blower, the gas that is ultimately provided to the patient may be provided at too high a pressure and/or the control algorithms of the ventilator may malfunction due to the high pressure gas provided at the inlet of the blower. With the slight pressure increase of the present technology, the blower and ventilator are substantially unaffected with the exception of being able to deliver a higher oxygen concentration.

In some examples, the targeted pressure may also be slightly less than ambient pressure. In such examples, the oxygen valve 104 opens only to charge the plenum 106 when a slightly negative pressure, caused by blower inlet vacuum, is sensed. For example, when the blower is activated, gas is drawn from the plenum 106 and may create a pressure within the plenum 106 that is less than the ambient pressure. In examples, where a slightly negative pressure triggers opening of the oxygen valve 104, a check valve may be included downstream of the plenum 106 and upstream of the mixing valve 108. The check valve prevents the flow of ambient air backwards through the mixing valve 108 and into the slight vacuum that exists in the plenum 106. For example, the targeted pressure may be between about 0.0 to −0.1 inH$_2$O or 0.0 to −0.2 inH$_2$O. Other target pressures may be used. When a breath is being delivered by the ventilator causing the blower to ramp up in speed, the pressure at the blower inlet is a slight vacuum of perhaps 1 inH$_2$O. The pressure sensor 110 detects that the pressure in the plenum 106 is below the target pressure, and the control device 112 sends a signal to the oxygen valve 104 to open, which charges the plenum 106.

The control loop includes a control device 112. The control device 112 receives pressure measurements, from the pressure sensor 110, of the pressure of gas in the plenum 106. Based on the pressure measurements received from the pressure sensor 110, the control device 112 generates a control signal to change the position of the valve 104. For example, if the gas pressure drops below the targeted pressure, the control device 112 generates a control signal to open the valve to allow more oxygen to flow into the plenum 106. In contrast, if the gas pressure increases above the targeted pressure, the control device 112 generates a control signal to close the valve to reduce or cease the flow of oxygen into the plenum 106 from the oxygen source 102. The control device 112 is communicatively coupled to the valve 104 to allow for control signals generated from the control device 112 to be sent to the valve 104.

In examples where valve 104 is a PSOL valve or other proportional valve where the position of the valve 104 may be set between fully open and fully closed positions, the control signal from the control device 112 may cause the valve 104 to open or close in amount less than the full range of the valve 104. In examples, where the valve 104 is either fully open or fully closed, the control signal from the control device 112 may cause the valve 104 to fully open or fully close. For such two-position valves that are either fully open or fully closed, a hysteresis loop may be implemented to prevent constant or rapid switching between states. In such examples, the hysteresis band may be about 0.1 in$H_2$O or 0.05 in$H_2$O around the targeted pressure of the gas in the plenum 106. Accordingly, no matter the type of valve 104 used, the valve 104 may be controlled by the control device 112 to maintain a targeted pressure of gas within the oxygen plenum. In some examples, control loop is relatively fast, and the control device 112 may process pressure measurements and generate valve control signals one every millisecond or faster.

In some implementations, a proportional valve, such as a PSOL, may be preferable to allow for more accurate control of the pressure in the plenum 106. In addition, the use of a proportional valve help prevents rapid full closings and openings of the valve 104, which may cause metal components of valve to impact one other with a large amount of force. Such impacts may be disfavored in an oxygen-rich environment.

The control device 112 may include a memory 114 and at least one processor 116. For example, the memory 114 may store instructions that, when executed by the processor 116, causes the control device 112 to perform the operations described herein. In some examples, the control device 112 may be a miniature computer or microcontroller, such as an ARDUINO NANO microcontroller available from the Arduino AG or Somerville, Massachusetts. In other examples, the control device 112 may be an integrated circuit (IC), programmable logic device (PLD), or a field-programmable gate array (FPGA), among other possible configurations or implementations. The control loop may also be a proportional-integral-derivative (PID) loop and control device 112 may be a PID controller.

The mixing valve 108 may be used to mix the oxygen from the plenum 106 with ambient air to achieve a desired oxygen concentration. The mixing valve 108 may include a first inlet to receive oxygen from the plenum 106 and a second inlet that is open to ambient air. The mixing valve 108 causes the oxygen from the plenum 106 to mix with ambient air, and the mixing valve 108 provides the gas mixture through at outlet that is configured to be coupled to a blower inlet of a ventilator. As an example, a dial may be connected to the mixing valve 108 that allows for various oxygen concentration levels to be selected or set. By moving the dial to increase the oxygen concentration level, the mixing valve is adjusted to increase the flow of oxygen from the plenum 106 as compared to the flow of ambient air. Such an adjustment may be achieved by altering the area of an aperture coupling the plenum 106 to output of the mixing valve 108 as compared an area of an aperture coupling the ambient air to the output of the mixing valve 108. In some examples, the mixing valve 108 may be controlled electronically based on a desired oxygen concentration level. The desired oxygen concentration level may be received as a signal from the ventilator, the control device 112, or another device that is capable of receiving a desired oxygen concentration level as an input and generate a signal corresponding to that concentration level to control the mixing valve 108.

In operation, when the system is connected to a blower of ventilator, the blower may initiate to provide a breath to a patient connected to the ventilator. The blower may include a fan that spins for a duration and speed based on the characteristics of the breath to be delivered to the patient, such as tidal volume, pressure targets, flow targets, etc. When the blower is activated, the gas mixture from the mixing valve 108 drawn through the inlet of the blower. When the gas mixture is drawn through the mixing valve 108, the pressure of gas in the plenum 206 decreases. The decrease in pressure is measured by the pressure sensor 110, and the corresponding pressure measurement is provided to the control device 112. The control device 112 then generates a control signal to cause the valve 104 to open, at least partially, to allow oxygen to flow from the oxygen source 102 into the plenum 106 to raise the pressure.

Of note, the system 100 may be compatible with blowers that are rated to handle the maximum oxygen concentration, such as 100% oxygen, that is to be provided by the system 100 to the blower. If the blower is not rated to handle oxygen-rich inputs, risk of combustion may increase.

Figure 2:
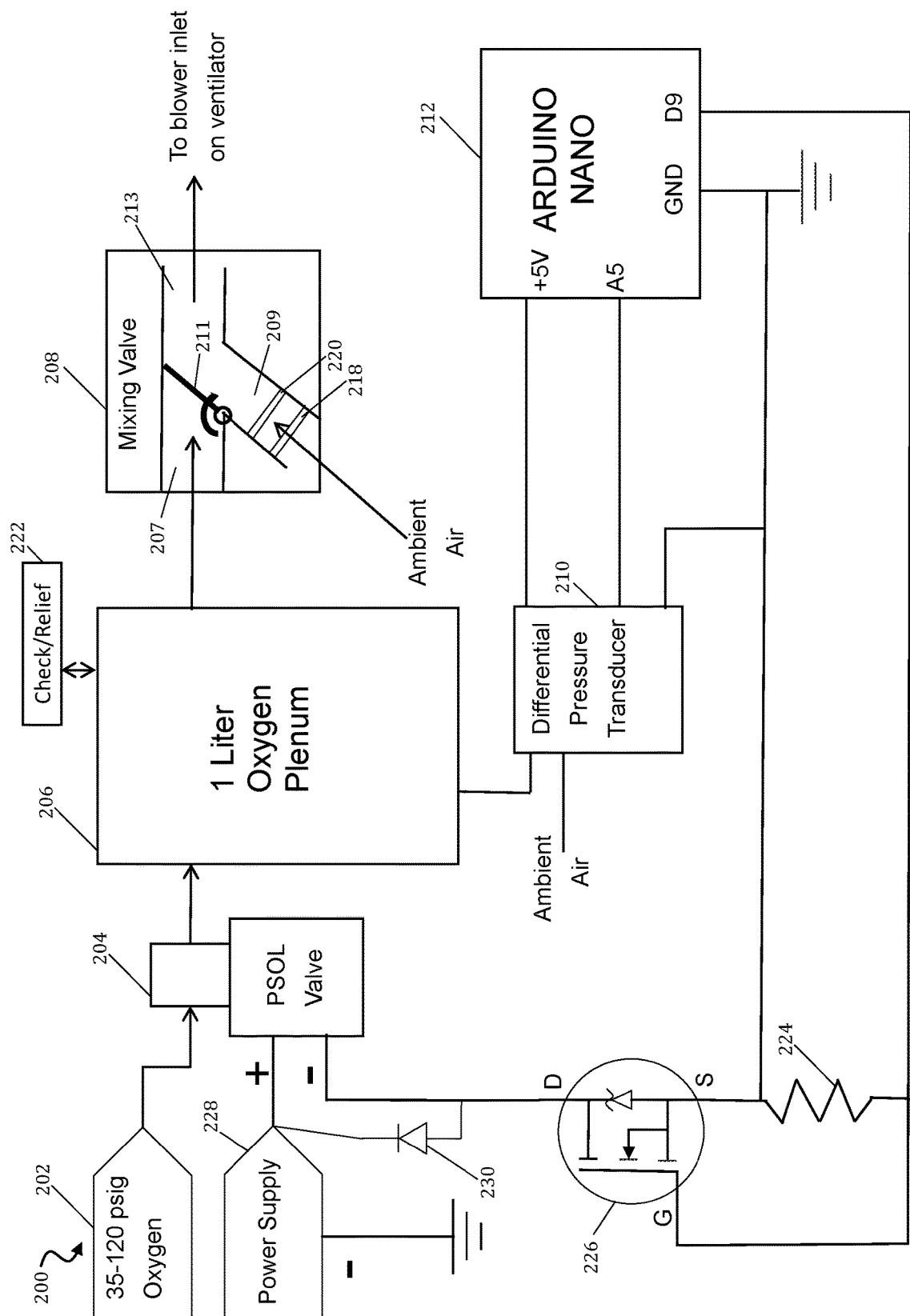
FIG. 2 depicts another example system for increasing oxygen concentration.

FIG. 2 depicts another example system 200 for increasing oxygen concentration. System 200 is a specific example implementation of the system 100 discussed above and depicted in FIG. 1. System 200 includes PSOL valve 204 that controls the flow of oxygen from an oxygen source 202 to an oxygen plenum 206. The oxygen source 202 may provide oxygen at a pressure between 35-120 pounds per square inch gauge (psig). A regulator may also be incorporated into, or connected to, the oxygen source 202 to regulate the pressure provided by the oxygen source 202. In examples where a proportional valve is used, such as PSOL valve 204, a regulator may not be necessary because the PSOL valve 204 may be set to have a small or large opening to account for a wide variety of input pressures from the oxygen source 202. The PSOL valve may be powered by a power supply 228. In the example depicted, the positive terminal of the power supply is connected to the PSOL valve 204 and the negative terminal of the power supply is connected to ground.

The oxygen plenum 206 in the example may have a volume of about one liter, but the volume of the plenum 206 may change in different examples. The size of the plenum 206 may be based on the tidal volumes that are to be provided by the ventilator. The size of the plenum 206 may also be based on the pressure available from the oxygen source 202. In some examples, it may be desirable to maintain a saturation of the plenum 206 with oxygen, and the plenum 206 may be sized accordingly.

An outlet of the plenum 206 is coupled to an oxygen inlet 207 of a mixing valve 208. The mixing valve 208 also includes an ambient-air inlet 209 that is open to ambient air. The mixing valve 208 also includes an outlet 213 to provide a mixture of gas to a blower inlet of a ventilator. The mixing valve 208 in the example depicted in FIG. 2 is a manual mixing valve. The mixture of oxygen from the oxygen inlet 207 and ambient air from the ambient-air inlet 209 may be controlled by rotating a valve member 211, which may be a "flapper." By rotating the valve member 211, the area of the aperture between inlet 207 and outlet 213 is altered at the same time as the area of the aperture between inlet 209 and outlet 213. Accordingly, the mixture of oxygen and ambient air (e.g., the oxygen concentration of the gas mixture) that is provided through the outlet 213 may be adjusted by rotating the valve member 211. In some examples, the valve member 211 may be manually rotated by a rotating a dial. The dial may have a plurality of settings that correspond to the oxygen concentration of the gas mixture provided at the outlet 213 of the mixing valve 208. Each setting of the dial causes the valve member 211 to be positioned such that the mixing valve 208 provides the set oxygen concentration. The mixing valve 208 may also be of the "spool valve" type, where the linear action of a shaft moves a spool across the ports of a 3-port valve to achieve the same mixing function.

In some examples, the ambient-air inlet 209 may also include an air filter 218 to filter the ambient air. The ambient-air inlet 209 may also include a check valve 220 that prevents the flow of oxygen from the plenum 206 through the ambient-air inlet 209. In some examples, the check valve 220 may be omitted. Even with the check valve 220 omitted, the amount of oxygen that flows out of the ambient-air inlet 209 is limited due to the relatively small pressure differential between the gas in the plenum 206 and ambient air. In examples where the check valve 220 is included, a check and/or relief valve 222 may also be connected to the plenum 206 to prevent over-pressurization or under-pressurization of the plenum 206. Over-pressurization of oxygen may introduce undesired hazards, impact the control algorithms of the ventilator, and/or impact the pressure, flow, and/or tidal volume of the breath delivered to the patient. In some examples, the check and/or relief valve 222 may be set to relieve any gas pressure above 5 cmH$_2$O in the plenum 206 over ambient air pressure. Similarly, the check and/or relief valve 222 may be set to allow gas to flow into the plenum 206 if the pressure of the gas in the plenum 206 is less than 5 cmH$_2$O below ambient air pressure.

The system 200 also includes a differential pressure transducer 210. The differential pressure transducer measures a differential pressure between the pressure of the ambient air and the pressure of the gas in the plenum 206. The transducer 210 includes an input for ambient air, which may be a port open to ambient air. The transducer 210 also includes an input that is pneumatically coupled to the plenum 206 to allow for the pressure differential to be measured by the transducer 210. The measured differential pressure between the ambient air and the gas in the plenum 206 is provided from the transducer 210 to a control device 212. As a specific example, the transducer 210 may be a P993 pressure sensor available from Sensata Technologies of Attleboro, Massachusetts.

In the example depicted, the control device 212 is an ARDUINO NANO. The transducer 210 may be connected to the +5V pin and an input pin, such as the A5 pin, of the control device 212. The transducer 210 and the control device 212 may also be connected to a common ground. The control device 212 operates as discussed above. For example, based on the measured differential pressure, a control signal is generated to either cause the PSOL valve 204 to move towards a closed position or an open position. To provide the control signal to the PSOL valve, an output of the control device, such as output in D9 of the ARDUINO NANO, may be coupled to a gate (G) of a transistor 226. The drain (D) of the transistor 226 is then coupled to the negative terminal of the PSOL valve 204, and the source (S) of the transistor 226 is connected to ground. The transistor 226 may be an N-channel MOSFET. As a specific example, the transistor may be a STD12NF06L-1 Power MOSFET available from STMicroelectronics of Geneva, Switzerland. The source (S) and gate (G) may also be connected by a resistor 224. In a specific example, the resistor may have a resistance of 56 kΩ. A recovery diode or rectifier 230 may be included between the positive and negative inputs of the PSOL valve 204. In a specific example, the rectifier 230 may be a 1N4005 recovery diode available from ON Semiconductor of Phoenix, Arizona.

Figure 3:
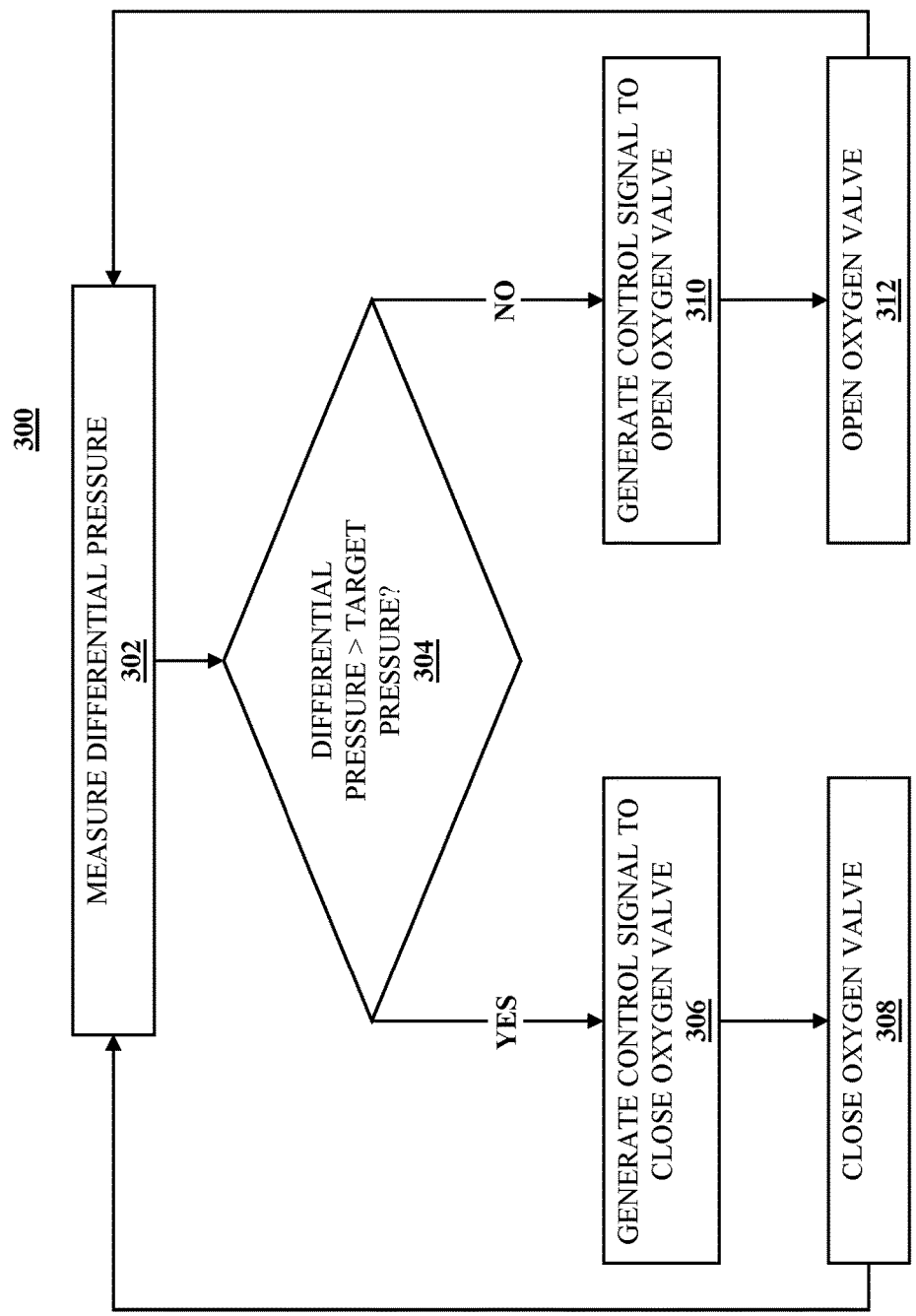
FIG. 3 depicts an example method for increasing oxygen concentration.

FIG. 3 depicts an example method 300 for increasing oxygen concentration to be provided to a blower inlet of a ventilator. At operation 302, a differential pressure between ambient air and gas inside the oxygen plenum is measured. The differential pressure may be measured by a pressure sensor. At operation 304, a determination is made as to whether the measured differential pressure is greater than a target pressure for the gas in the oxygen plenum. The determination may be made by a control device. If the differential pressure is determined to be greater than the target pressure in operation 304, method 300 flows to operation 306 where the control device generates a control signal to close the oxygen valve that controls flow of oxygen from the oxygen source into the oxygen plenum. The control signal may be configured to entirely close the valve or partially close the oxygen valve. At operation 308, the oxygen valve receives the control signal and closes according to the control signal. After operation 308, method 300 flows back to operation 302 where the method 300 repeats.

If the differential pressure is determined to not be greater than the target pressure in operation 304, method 300 flows to operation 310 where the control device generates a control signal to open the oxygen valve. At operation 312, the oxygen valve receives the control signal and opens according to the control signal. After operation 308, method 300 flows back to operation 302 where the method 300 repeats.

Figure 4:
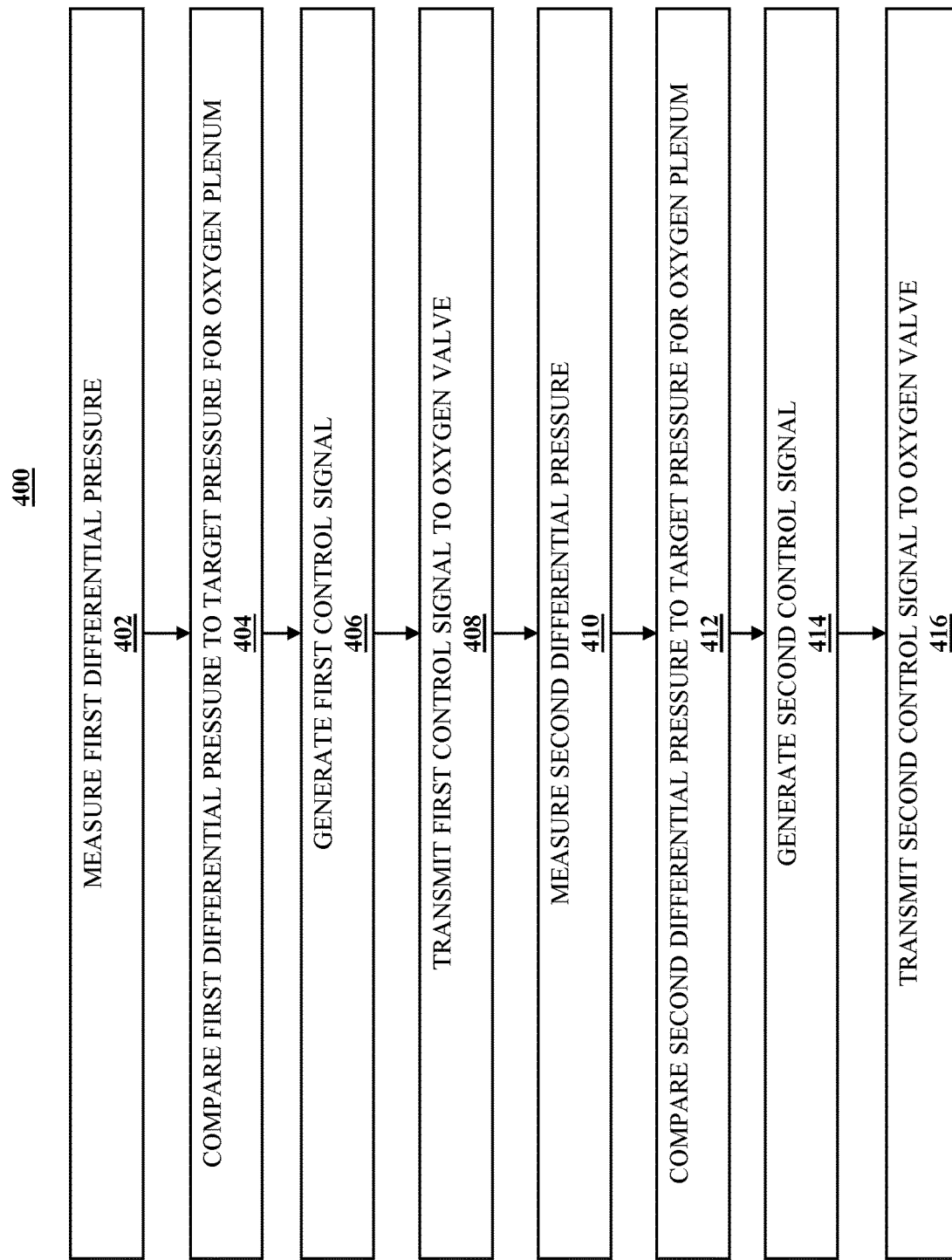
FIG. 4 depicts another example method for increasing oxygen concentration.

FIG. 4 depicts another example method 400 for increasing oxygen concentration to be provided to a blower inlet of a ventilator. At operation 402, a first differential pressure between ambient air and gas in an oxygen plenum is measured by a pressure sensor. At operation 404, the measured first differential pressure is compared, by a control device, to a target pressure for the oxygen plenum. At operation 406, a first control signal for an oxygen valve is generated by the control device. Generation of the first control signal is based on the first differential pressure and/or the comparison performed in operation 404. At operation 408, the first control signal is transmitted to the oxygen valve to cause the oxygen valve to change position to affect flow of oxygen into the oxygen plenum. As an example, if the comparison in operation 404 indicates that the first differential pressure is less than the target pressure, the first control signal is configured to cause the oxygen valve to open.

At operation 410 a second differential pressure between ambient air and gas in an oxygen plenum is measured by the pressure sensor. The second differential pressure may be measured immediately after the first differential pressure measurement or at a substantial time (e.g., greater than 5 seconds) after the first differential pressure measurement. Accordingly, additional differential pressure measurements may, or may not, occur between the first pressure differential measurement and the second pressure differential measurement. At operation 412, the measured second differential pressure is compared, by the control device, to the target pressure for the oxygen plenum. At operation 414, a second control signal is generated by the control device. Generation of the second control signal is based on the second differential pressure and/or the comparison performed in operation 412. At operation 416, the second control signal is transmitted to the oxygen valve to cause the oxygen valve to change position to affect flow of oxygen into the oxygen plenum.

The embodiments described herein may be employed using software, hardware, or a combination of software and hardware to implement and perform the systems and methods disclosed herein. Although specific devices have been recited throughout the disclosure as performing specific functions, one of skill in the art will appreciate that these devices are provided for illustrative purposes, and other devices may be employed to perform the functionality disclosed herein without departing from the scope of the disclosure. In addition, some aspects of the present disclosure are described above with reference to block diagrams and/or operational illustrations of systems and methods according to aspects of this disclosure. The functions, operations, and/or acts noted in the blocks may occur out of the order that is shown in any respective flowchart. For example, two blocks shown in succession may in fact be executrix or performed substantially concurrently or in reverse order, depending on the functionality and implementation involved.

This disclosure describes some embodiments of the present technology with reference to the accompanying drawings, in which only some of the possible embodiments were shown. Other aspects may, however, be embodied in many different forms and should not be construed as limited to the embodiments set forth herein. Rather, these embodiments were provided so that this disclosure was thorough and complete and fully conveyed the scope of the possible embodiments to those skilled in the art. Further, as used herein and in the claims, the phrase "at least one of element A, element B, or element C" is intended to convey any of: element A, element B, element C, elements A and B, elements A and C, elements B and C, and elements A, B, and C. Further, one having skill in the art will understand the degree to which terms such as "about" or "substantially" convey in light of the measurements techniques utilized herein. To the extent such terms may not be clearly defined or understood by one having skill in the art, the term "about" shall mean plus or minus ten percent.

Although specific embodiments are described herein, the scope of the technology is not limited to those specific embodiments. Moreover, while different examples and embodiments may be described separately, such embodiments and examples may be combined with one another in implementing the technology described herein. One skilled in the art will recognize other embodiments or improvements that are within the scope and spirit of the present technology. Therefore, the specific structure, acts, or media are disclosed only as illustrative embodiments. The scope of the technology is defined by the following claims and any equivalents therein.

What is claimed is:

1. A system for increasing oxygen concentration, the system comprising:
    an oxygen valve configured to be coupled to an oxygen source;
    an oxygen plenum coupled to the oxygen valve; and
    a mixing valve comprising:
        an oxygen inlet coupled to the oxygen plenum;
        an ambient-air inlet, wherein the ambient-air inlet of the mixing valve further comprises a check valve; and
        an outlet configured to be attached to an inlet of a blower of a ventilator.

2. The system of claim 1, wherein the oxygen valve is a proportional valve.

3. The system of claim 1, wherein the mixing valve is one of a manual mixing valve or an electromechanical mixing valve controlled by a signal from a microprocessor based on a user setpoint.

4. The system of claim 1, further comprising a dial to control the mixing valve, wherein different settings of the dial correspond to different oxygen concentrations provided at the outlet of the mixing valve.

5. The system of claim 1, further comprising a pressure sensor coupled to the oxygen plenum.

6. The system of claim 5, wherein the pressure sensor is configured to measure a differential pressure between gas in the oxygen plenum and ambient air.

7. The system of claim 6, further comprising a control device, the control device configured to perform a set of operations including:
    receiving the differential pressure measured by the pressure sensor; and
    based on the measured differential pressure, generating a control signal to control the oxygen valve to maintain a target pressure of gas within the oxygen plenum.

8. The system of claim 7, wherein:
    when the measured differential pressure is below the target pressure, the control signal causes the oxygen valve to open.

9. The system of claim 7, wherein:
    when the measured differential pressure is above the target pressure, the control signal causes the oxygen valve to close.

10. The system of claim 7, wherein the target pressure is less than or equal to 0.5 $inH_2O$.

11. The system of claim 1, wherein the check valve prevents flow of oxygen from the oxygen plenum through the ambient-air inlet.

12. The system of claim 11, further comprising at least one of a check valve or a relief valve coupled to the oxygen plenum to relieve gas pressure in the oxygen plenum.

13. A system for increasing oxygen concentration, the system comprising:
    an oxygen valve configured to be coupled to an oxygen source;
    an oxygen plenum coupled to the oxygen valve;
    a mixing valve comprising:
        an oxygen inlet coupled to the oxygen plenum;
        an ambient-air inlet, wherein the ambient-air inlet of the mixing valve further comprises a check valve; and
        an outlet configured to be attached to an inlet of a blower of a ventilator;
    a pressure sensor coupled to the oxygen plenum, the pressure sensor configured to measure a differential pressure between gas in the oxygen plenum and ambient air; and
    a control device communicatively coupled to the pressure sensor and the oxygen valve, the control device configured to perform a set of operations including:
        receiving the differential pressure measured by the pressure sensor; and
        based on the measured differential pressure, generating a control signal to control the oxygen valve to maintain a target pressure of gas within the oxygen plenum.

14. The system of claim 13, wherein:
    when the measured differential pressure is below the target pressure, the control signal causes the oxygen valve to open.

15. The system of claim 13, wherein:
    when the measured differential pressure is above the target pressure, the control signal causes the oxygen valve to close.

16. The system of claim 13, wherein the target pressure is less than or equal to 0.5 inH$_2$O.

* * * * *